United States Patent [19]

Aigner

[11] Patent Number: 4,563,170
[45] Date of Patent: Jan. 7, 1986

[54] DEVICE FOR IN VIVO PURIFICATION OF BLOOD

[76] Inventor: Karl Aigner, 6301 Pohlheim 1, Fed. Rep. of Germany

[21] Appl. No.: 518,449

[22] Filed: Jul. 29, 1983

[30] Foreign Application Priority Data

Jul. 30, 1982 [DE] Fed. Rep. of Germany ....... 3228438

[51] Int. Cl.$^4$ .............................................. A61M 1/03
[52] U.S. Cl. ......................................... 604/5; 604/27; 604/43
[58] Field of Search ...................... 604/5, 4, 6, 27, 39, 604/43, 44

[56] References Cited

U.S. PATENT DOCUMENTS

| | | | |
|---|---|---|---|
| 3,811,800 | 5/1974 | Shill | 604/5 X |
| 3,995,617 | 12/1976 | Watkins et al. | 604/4 X |
| 4,047,526 | 9/1977 | Reynolds et al. | 604/4 |
| 4,231,366 | 11/1980 | Schael | 604/4 |
| 4,300,550 | 11/1981 | Gandi et al. | 604/45 |
| 4,385,631 | 5/1983 | Uthmann | 604/43 |
| 4,416,280 | 11/1983 | Carpenter et al. | 604/4 X |

Primary Examiner—Stephen C. Pellegrino
Attorney, Agent, or Firm—Keil & Weinkauf

[57] ABSTRACT

Device for in-vivo purification of the blood, with which blood pumped from a vein is subjected to intensive ultrafiltration and the filtrate, together with a quantity of the substitution fluid volumetrically corresponding to the filtrate, is returned to the vein, which device combines a double lumen catheter, an inserted, initial tube pump, and an ultrafiltration filter, with connecting tubes between catheter and pump. A feed line, with an inserted, second pump for the substitute fluid, opens into the return line from the hemofilter to the catheter, and a feed line for anticoagulants opens into the feed line to the first tube pump; the ultrafilatration filter is also connected through a precisely adjustable valve to a measuring container in which the fluid drawn out of the system is collected. The device is particularly suited for the filtration of venous blood in intraaterial chemotherapy, the chemotherapeutic agents, particularly cytostatic drugs, being filtered out before they reach the heart, so that toxic secondary effects do not arise.

4 Claims, 5 Drawing Figures

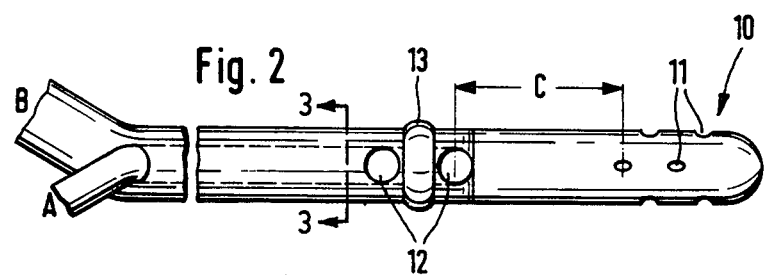
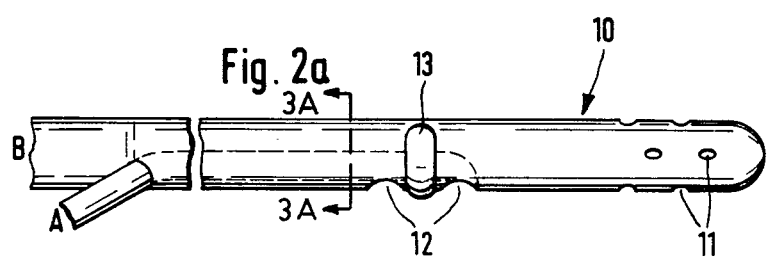
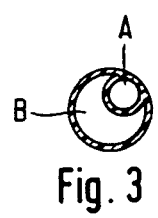
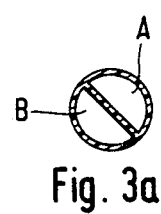

DEVICE FOR IN VIVO PURIFICATION OF BLOOD

BACKGROUND OF THE INVENTION AND PRIOR ART

The object of the invention is a device for the in vivo purification of blood, with which blood pumped out of a vein is subjected to intensive ultrafiltration, the filtrate being reintroduced into the vein along with a corresponding volume of a substitute fluid. The device is particularly suited for filtering out substances introduced in high concentrations in intraarterial chemotherapy before the venous blood enters the heart and the systemic circulation.

The ultrafiltration of human blood in the case of kidney failure, whose object is to achieve a kidney replacement function, is well-known. The blood is withdrawn from an artery and under its own pressure is conducted through an ultrafilter or a so-called hemofilter and the filtrate is returned to a vein, under certain conditions along with a substitute fluid.

In intraarterial chemotherapy, particularly in the treatment of tumors, it is desirable to apply the appropriate chemotherapeutic agents to the area of treatment in the highest possible concentration. In the past toxicity and other secondary effects have limited compatability and thus too the maximum possible dosage.

OBJECT AND SUMMARY OF THE INVENTION

The objective of the present invention is to create a device for in-vivo purification of the blood which enables large quantities of therapeutically effective substances introduced in the process of intraarterial chemotherapy to be filtered out of the venous blood in order to eliminate toxic effects and secondary reactions.

This objective is achieved by a device for the in-vivo purification of the blood with catheters, an ultrafiltration filter, a tube pump, and a tube connection between the catheters, the tube pump, and the ultrafiltration filter. The device combines (a) a double lumen catheter (10) with attaching tube connection (8, 9), the tube (8) being connected from the catheter part (A) to the inlet side of the ultrafiltration filter (1) by way of a first intermediate pump (2), and the tube (9) connecting the outlet side of the ultrafiltration filter (1) for the return of the filtrate with the catheter part (B).

(b) a feed line with a second intermediate tube pump (2a) for substitute fluid, which opens into the tube connection (9) behind the filter (1)

(c) a feed line for the anticoagulants, which opens into the tube line (8) in front of the filter (1), and (d) the outflow line for the filtrate, which leads from the ultrafiltration filter (1) through a precisely adjustable valve (5) and terminates in a measuring tank 6.

To make possible the removal of blood from a vein, a double lumen catheter with a closed tip is employed. The catheter displays an initial catheter part with several openings arranged laterally in the area of the tip, and a second catheter part within the first part, which second part terminates with 2 or more openings in the outer wall of the catheter, the distance between the lateral opening furthest away from the catheter tip and the closest opening of the second catheter part being not less than 40 mm and not more than 50 mm.

The catheter has the form of a double tube, the first catheter part B serving as a return flow tube and the second catheter part A serving as a suction outlet tube. The sectional area of the two catheter parts can be of equal or differing size. When the sizes differ the sectional area of the second catheter part A is smaller than that of part B. The catheter can be effectively inserted from the groin into the vena cava inferior, until the catheter tip rests in the right atrium of the heart. When reintroducing the blood, in order to prevent disturbances caused by the blood flow which might, in turn, cause disturbances in the cardiac rhythm, the actual tip of the catheter is closed and the returned filtrate flows through several lateral openings.

It is essential that the suction point be no less than 40 mm and no more than 50 mm from the closest outlet opening.

The venous blood is sucked out with a tube pump or so-called roller pump and pumped through a conventional ultrafiltration filter under the increased pump pressure, and the (filtrate) is introduced into the first catheter part at a volume of 400–500 ml per minute. Since during filtration 100–200 ml per minute of filtrate fluid simultaneously leaves the ultrafiltration filter, it is necessary to counterbalance this loss by introducing a corresponding quanitity of substitute fluid. To make this possible the tube connection has an attachment for the substitute fluid, located between the ultrafiltration filter outlet for the filtrate and the catheter, a second tube pump being placed in the attachment line to feed the needed volume of substitute fluid into the system. A line connected to the filter passes through a precisely adjustable valve and terminates in a collecting container with a measuring capacity which volumetrically determines the quantity of fluid drawn out of the circulation system.

A feed line for anticoagulants, e.g. heparin, opens in the tube line between the suction tube pump and the catheter. This feed line, which is about 1 m in length, has an inner diameter of 1.5 mm and an outer diameter of 3 mm and is attached at its other end to a precisely adjustable automatic injection mechanism.

The ratio of the free sectional area of the first catheter part B to the second catheter part A is from 1:1 to 2:1. The inner diameter of the catheter tube is not less than 3 mm and is preferably 4 mm, so that the catheter has an outer diameter of about 4–5 mm.

The outlet openings of the first catheter part B are arranged at the catheter end over a distance of about 15–20 mm, and the openings have a diameter of from 1.5 to 4 mm. The openings in the second catheter part A, or suction tube, which is located inside the catheter, are preferably as large as the sectional area of the tube and are positioned at the already indicated distance from the last feed hole in the outer wall of the catheter. Preferably there are two suction openings, between which, on the outside of the catheter wall, there can be a bulge about 2 mm thick, which extends over half of the outer circumference of the catheter; this semicircular bulge assures that the suction openings will not be covered and sealed by the blood vessel wall. The double lumen catheter is about 60–80 cm long and preferably displays a marking 45 cm from the end of the catheter in order to better control the inserted length. On the back end of the catheter the two catheter parts are separated from each other, the first part displaying an attachment piece about 20 cm long and the second part one about 10 cm long.

The catheter is connected to the tube pump or ultrafiltration filter by means of tube connections; in front of the behind the first tube pump, which aspirates the blood and presses it into the filter, a rubber diaphragm is inserted into the tube connection to make injections possible, as well as the removal of control samples with a syringe. Further diaphragms of this type may be placed in the filtrate line, behind the ultrafiltration filter and in front of the valve, and in the tube connection for the filtrate to the catheter. In order to better control the pressure and the filling of the system, a pillow-shaped tube piece of elastic material can be positioned between the tube pump and the ultrafiltration filter; the tube piece enlarges under the pressure produced by the tube pump, and its increase or diminution in volume provides a scale for the pressure produced by the pump and for the filling of the system.

The positioning of a further pillow-shaped tube piece in the tube line for the filtrate to the catheter is of special advantage for observation of the degree of filling.

The pillows also function as air bubble traps.

To equalize heat losses caused by cooling within the device, a preferred embodiment provides for the insertion of a 3-7 m, preferably 5 m, long spiral tube in the return tube line, the spiral tube being placed in a water bath with a temperature of 40° C. This makes it possible to heat the filtered blood and the introduced substitute fluid to the desired body temperature. The catheter can be produced of conventional materials suitable for catheters. Such materials have a neutral behavior toward the body fluid, can be sterilized without difficulty, and are sufficiently elastic, but also sufficiently rigid and solid to be introduced into the blood vessels. Suitable materials are polyolefins, polyfluoridated hydrocarbon polymers, synthetic rubbers, polyvinyl chloride, and the like. Specially preferred catheter materials are silicon rubber and implantable polyvinyl chloride. Basically comparable materials are suitable for the tube connections, particularly polyolefins, fluoridated hydrocarbon polymers or polyvinyl chloride. The tube pumps are conventional tube pumps or so-called roller pumps, in which the pump effect is produced by compression of the tube.

Conventional ultrafiltration filters, with conventional diaphragms, are suitable as ultrafiltration filters, to the extent that the filter area and filter capacity are sufficient to remove the necessary amount of low-molecular products from the blood. The necessary filter area is on an order of 1–2.5 $m^2$, preferably 1.4–2.0 $m^2$; a filter area of 2 $m^2$ is particularly preferred. Suitable diaphragms are those that admit substances with a molecular weight of from 40,000 to 60,000, while blocking substances with a higher molecular weight. In special cases other diaphragms can be employed, which admit only low-molecular products up to a weight of 20,000.

The invention device is particularly suited for use in cytostatic drug filtration in intraarterial chemotherapy and allows for systemic treatment with high local concentrations; after taking effect, the cytostatic drugs and other therapeutically active substances are filtered out of the blood by means of an ultrafilter, thus preventing toxic side effects, which particularly tend to arise when these substances reach the heart with the blood and then enter the bodily system.

BRIEF DESCRIPTION OF THE DRAWINGS

The invention is described in greater detail on the basis of the illustrations.

FIGS. 2 and 2a show the form of the catheter;

FIGS. 3 and 3a show a cross-section of the catheter, from which the arrangement of the second catheter part within the first catheter part can be identified.

DETAILED DESCRIPTION OF THE PREFERRED EMBODIMENTS

Figure 1:
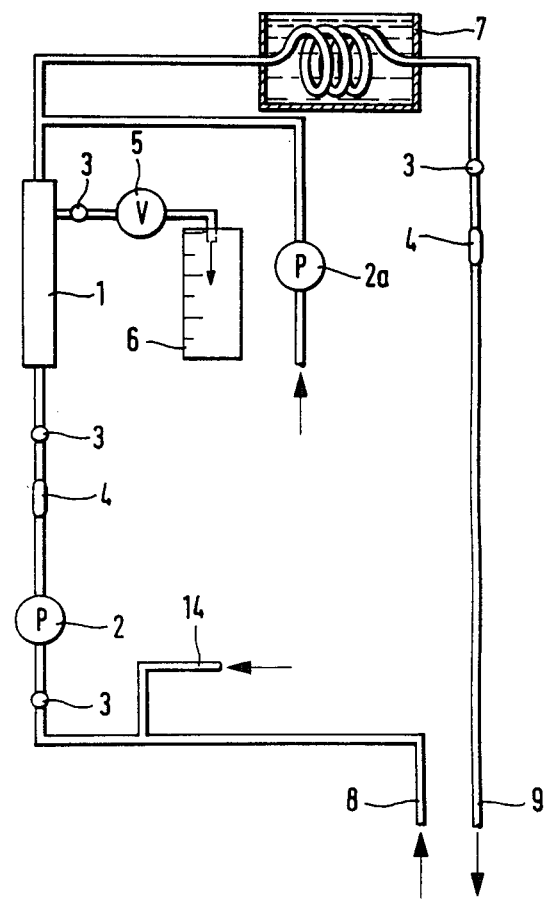
FIG. 1 shows a schematic overview of the invention device.

FIG. 1 shows a schematic overview of the invention device, the connecting tubes 8, 9 of the double lumen catheter shown in FIG. 2 being arranged in such a way that the suction line is attached to tube 8 and the return line is attached to tube 9. Venous blood is aspirated by tube pump 2 from the second catheter part A through connecting tube 8 and pressed through the attached tube into the ultrafiltration filter 1, to reach connecting tube 9 to the first catheter part B. In front of the filter 1 the feed line 14 for anticoagulants opens into the connecting tube 8; the feed line 14 runs from an automatic injection apparatus. Rubber diaphragms 3 are inserted into the connecting tube 8 in front of and behind the tube pump 2 to allow injections to be made and control samples to be withdrawn with hypodermic needles. The same diaphragms are positioned in the filtrate line between filter 1 and valve 5 and in the tube line 9 behind the spiral tube 7 positioned in the water bath.

4 indicates the elastic rubber pillows for filling control. A line runs from ultrafilter 1 and contains the precisely adjustable valve 5 and terminates in a measuring vessel 6 for collecting the fluid drawn out of the circulation system. The measuring container is equipped with an indicator scale and has a capacity of 1-3 liters. In the connecting tube 9, behind the ultrafiltration filter, there is a feed point for the substitute fluid, which is fed by a second tube pump 2a. The tube pump 2a aspirates the substitute fluid from one or several supply containers of appropriate size attached by means of connection tubes. If necessary the connecting tube can contain forks that enable the use of several different substitute fluids. Pumping of the substitute fluids, which perferably are so-called Ringer's solutions, is necessary inasmuch as the large volume of substitute fluid cannot otherwise be introduced into the system with the desired precision and speed. The output of the second tube pump 2a is regulated according to the quantity of fluid leaving the system through the adjustable valve 5, such that a volumetric loss of fluid is avoided. In principle, however, it is also possible to introduce smaller or larger quantities of substitute fluid, if this is required in special cases by the overall therapy.

To equalize cooling losses a spiral tube 7 is placed in tube line 9; the spiral tube is located in a water bath with a temperature of about 40° C. This compensates in a simple fashion for heat losses, allowing the filtrate to be returned to the vein at the desired temperature after filtration. The connecting tube between the catheter and the tube pump has a length of about 1.5 meters; the tube length between the tube pump and the filter is about 1 m, and about 2 m of connecting tube, without the spiral tube, is necessary to attach tube 9 to the catheter. The connecting tubes have an inner diameter of about 5 mm and an outer diameter of about 7 mm.

FIG. 2 shows the double lumen catheter 10 from the side, with the closed end of the first catheter part B and the lateral openings 11. The second catheter part A, which terminates with the openings 12 in the catheter wall, is located on the inside of the first catheter part B.

The distance C between the opening 12, serving as a suction opening, and the closest return opening 11 in the first catheter part B is not less than 40 mm and not more than 50 mm. In a preferred embodiment there is a semi-circular bulge between two suction openings 12 on the outside of the catheter wall, to prevent the blood vessel wall from resting on the catheter and to prevent closing of the suction openings.

FIG. 2a shows a top view of the catheter, with the lateral suction openings 12 and the return openings 1 of the first catheter part B arranged at intervals along the catheter point.

FIGS. 3 and 3a show possible embodiments of the fitting catheter parts A and B, the form shown in FIG. 3 being preferred, in which a second tube A with a smaller sectional area is arranged inside a first tube B. The ratio of the sectional areas B:A is preferably 1:1, i.e. the total sectional area of the catheter is twice the area of the catheter part A. In the embodiment shown in FIG. 3a the inside of the catheter has a separating wall, which separates catheter parts A and B.

LIST OF THE REFERENCE NUMERALS 1 ultrafilter, hemofilter
2,2a tube pumps
3 rubber diaphragms
4 soft tubing for optical filling control, tube pillow
5 precisely adjustable valve
6 collecting container for withdrawn fluid (measuring container)
7 spiral tube in water bath
tube line from catheter
9 tube line to catheter
catheter
11,12 openings in catheter parts
13 bulge
tube line

I claim:

1. An in-vivo blood purification system for use in intra-arterial chemotherapy, said system comprising:
   a substantially cylindrical double-lumen catheter insertable into the vena cava up to the vicinity of the heart and being formed to provide therein a first channel (B) and, generally parallel thereto, a second channel (A), each said channel being at least partially bounded by the wall of said catheter, and the catheter having a closed tip and a plurality of openings (11) which are laterally positioned in the vicinity of the catheter tip and communicate with said first channel (B), and said second channel (A) terminating with at least two openings (12) in said wall of the catheter, the distance between the lateral opening (11) farthest from the catheter tip and the closest opening (12) of the second channel (A) being not less than 40 mm and not more than 50 mm, and the opening (12) at the end of the second channel (A) having the same size as the inner cross-sectional area of said channel (A);
   means (8, etc.) connected to said second channel (A) for pumping large amounts of blood out of the vena cava through said channel;
   means (1, etc.) for sujecting said blood to ultrafiltration; and
   means (9, etc.) connected to said first channel (B) for returning, simultaneously with the withdrawal of blood from said second channel (A), the filtrate to the vena cava through said first channel (B) together with a requisite amount of substitute fluid.

2. A system as claimed in claim 1, wherein the ratio of the cross-sectional areas of the first and second channels is from 1:1 to 2:1.

3. A system as claimed in claim 1, wherein the openings (12) at the end of the second channel (A) are as large as the cross-section of the second channel (A).

4. A system as claimed in claim 1, wherein a bulge (13) about 2 mm thick extends over half of the outer circumference of the catheter 10 between the openings (12) in the catheter wall.

* * * * *

UNITED STATES PATENT AND TRADEMARK OFFICE
CERTIFICATE OF CORRECTION

PATENT NO. : 4,563,170
DATED : Jan. 7, 1986
INVENTOR(S) : Karl Aigner

It is certified that error appears in the above-identified patent and that said Letters Patent are hereby corrected as shown below:

| | | | |
|---|---|---|---|
| Column 3, | line 3 | "the behind" should be -- and behind -- . |
| "   5, | "  11 | "openings 1" should be -- openings 11 -- . |
| "   ", | "  34 | insert -- 8 -- before "tube" . |
| "   ", | "  36 | insert -- 10 -- before "catheter". |
| "   ", | "  39 | insert -- 14 -- before "tube". |

Signed and Sealed this

First Day of April 1986

[SEAL]

Attest:

DONALD J. QUIGG

Attesting Officer

Commissioner of Patents and Trademarks